(12) United States Patent
Amor et al.

(10) Patent No.: US 6,231,573 B1
(45) Date of Patent: May 15, 2001

(54) DEVICE FOR TREATING ANEURYSMS

(75) Inventors: Max Amor; Michel Henry, both of Nancy (FR)

(73) Assignee: Medicorp, S.A., Villers-les-Nancy (FR)

(*) Notice: Subject to any disclaimer, the term of this patent is extended or adjusted under 35 U.S.C. 154(b) by 0 days.

(21) Appl. No.: 09/086,545

(22) Filed: May 29, 1998

(30) Foreign Application Priority Data

Apr. 21, 1998 (EP) .................................... 98870089

(51) Int. Cl.$^7$ .................................... A61B 18/18
(52) U.S. Cl. .................... 606/49; 606/40; 606/213; 606/108
(58) Field of Search .................... 606/1, 27, 31, 606/41, 49, 108, 151, 213, 206

(56) References Cited

U.S. PATENT DOCUMENTS

| | | |
|---|---|---|
| 2,625,934 | 1/1953 | Halliday . |
| 4,425,908 | 1/1984 | Simon . |
| 4,503,569 | 3/1985 | Dotter . |
| 4,512,338 | 4/1985 | Balko et al. . |
| 4,580,568 | 4/1986 | Gianturco . |
| 4,655,771 | 4/1987 | Wallsten . |
| 4,665,906 | 5/1987 | Jervis . |
| 4,681,110 | 7/1987 | Wiktor . |
| 4,743,251 | 5/1988 | Barra . |
| 4,795,458 | 1/1989 | Regan . |
| 4,950,227 | 8/1990 | Savin et al. . |
| 4,954,126 | 9/1990 | Wallsten . |
| 5,026,377 | 6/1991 | Burton et al. . |
| 5,037,427 | 8/1991 | Harada et al. . |
| 5,061,275 | 10/1991 | Wallsten . |
| 5,067,957 | 11/1991 | Jervis . |
| 5,108,407 * | 4/1992 | Geremia et al. ............... 606/108 |
| 5,122,135 * | 6/1992 | Guglielmi et al. ............. 606/32 |
| 5,190,546 | 3/1993 | Jervis . |
| 5,197,978 | 3/1993 | Hess . |
| 5,201,901 | 4/1993 | Harada et al. . |
| 5,226,913 | 7/1993 | Pinchuk . |
| 5,261,916 * | 11/1993 | Engelson ..................... 606/108 |
| 5,304,195 * | 4/1994 | Twyford, Jr. et al. ......... 606/191 |
| 5,354,309 | 10/1994 | Schnepp-Pesch et al. . |
| 5,395,390 | 3/1995 | Simon . |
| 5,405,377 | 4/1995 | Cragg . |
| 5,423,829 * | 6/1995 | Pham et al. .................. 606/108 |
| 5,443,454 * | 8/1995 | Tanabe et al. ................ 604/264 |
| 5,480,423 | 1/1996 | Ravenscroft et al. . |

(List continued on next page.)

FOREIGN PATENT DOCUMENTS

| | | |
|---|---|---|
| 1205743 | 9/1970 | (EP) . |
| 01730848 | 2/1996 | (EP) . |
| 0740928 | 3/1996 | (EP) . |
| 0744164 | 5/1996 | (EP) . |
| 2048682 | 4/1980 | (GB) . |
| 9219310 | 11/1992 | (WO) . |
| 9530385 | 11/1995 | (WO) . |
| 9531945 | 2/1996 | (WO) . |
| 9604954 | 2/1996 | (WO) . |
| 9713475 | 4/1997 | (WO) . |
| 9719643 | 6/1997 | (WO) . |
| 9720530 | 6/1997 | (WO) . |
| 97/19643 * | 6/1997 | (WO) . |

Primary Examiner—Michael Peffley
(74) Attorney, Agent, or Firm—Roylance, Abrams, Berdo & Goodman, L.L.P.

(57) ABSTRACT

Device for treating lesions of the wall of blood vessels, in particular false aneurysms, by coagulation, which device comprises an introducer with value and with removable needle, a filament which is able to be introduced into the pocket of this aneurysm and to roll up on itself therein, and a introducing the said filament into the pocket through the introducer.

43 Claims, 4 Drawing Sheets

U.S. PATENT DOCUMENTS

| | | |
|---|---|---|
| 5,540,712 | 7/1996 | Kleshinski . |
| 5,540,713 | 7/1996 | Schnepp-Pesch et al. . |
| 5,554,181 | 9/1996 | Das . |
| 5,562,725 | 10/1996 | Schmidt et al. . |
| 5,562,728 | 10/1996 | Lazarus et al. . |
| 5,575,818 | 11/1996 | Pinchuk . |
| 5,597,378 | 1/1997 | Jervis . |
| 5,630,840 | 5/1997 | Mayer . |
| 5,643,278 | 7/1997 | Wijay . |
| 5,643,339 | 7/1997 | Kavteladze et al. . |
| 5,645,559 | 7/1997 | Hachtman et al. . |
| 5,649,949 * | 7/1997 | Wallace et al. ............... 606/191 |
| 5,674,277 | 10/1997 | Freitag . |
| 5,741,333 | 4/1998 | Frid . |
| 5,749,894 * | 5/1998 | Engelson ............... 606/213 |
| 5,891,155 * | 4/1999 | Irie ............... 606/108 |
| 5,911,717 * | 6/1999 | Jacobsen et al. ............ 606/1 |
| 5,935,148 * | 8/1999 | Villar et al. ............ 606/213 |

* cited by examiner

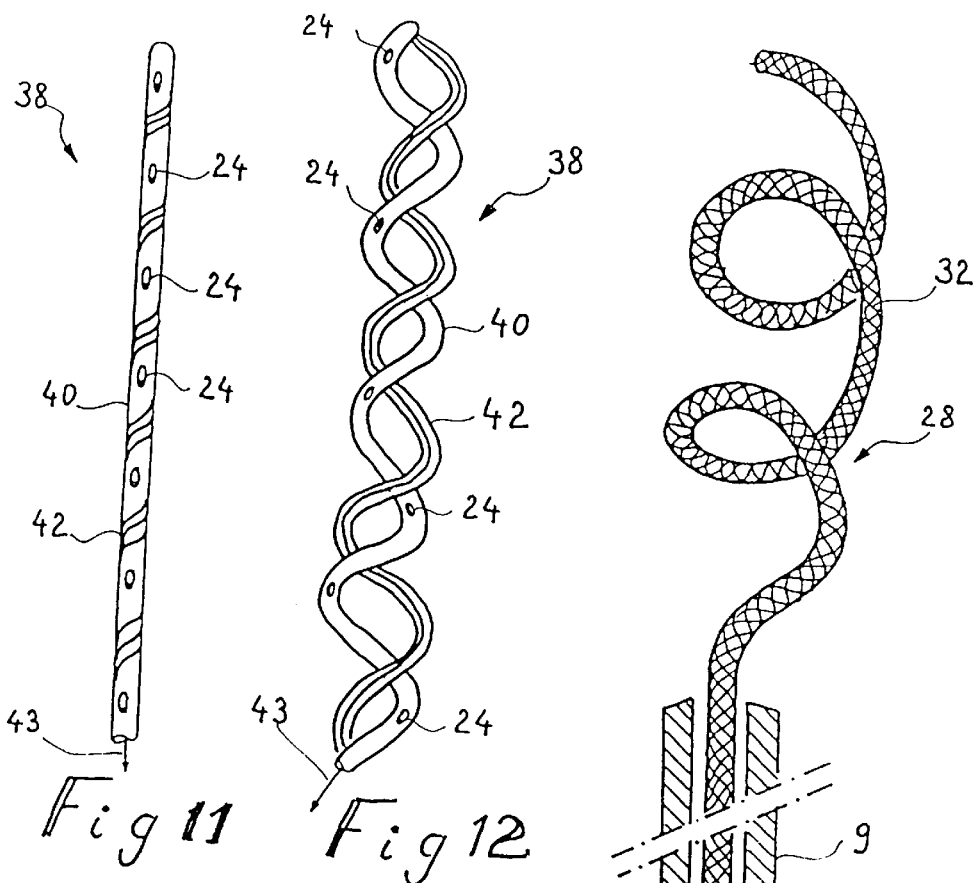
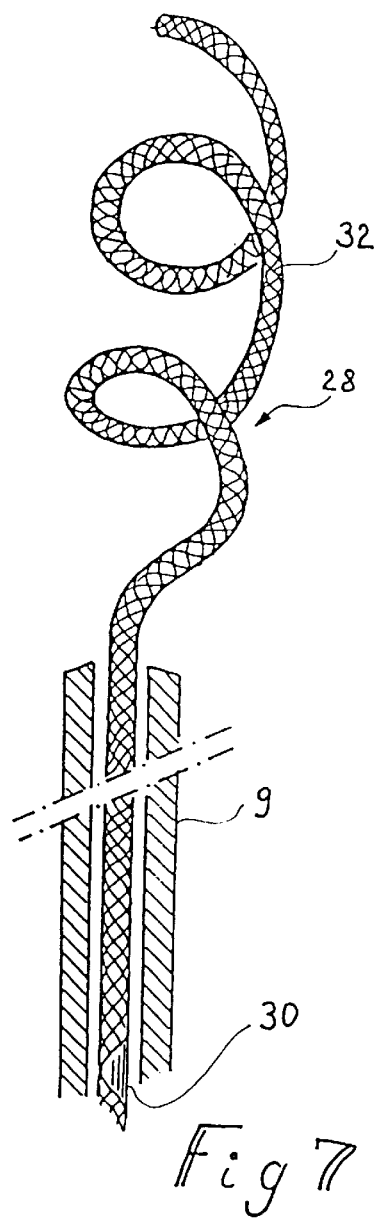
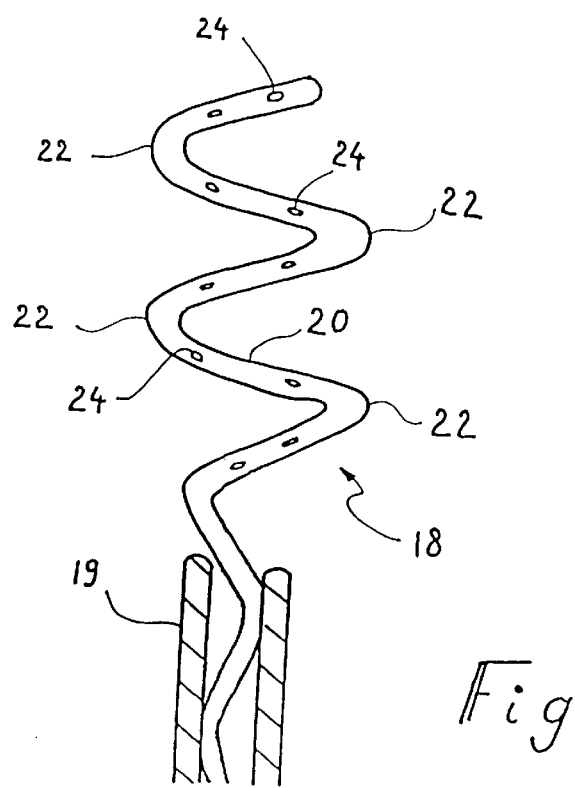
Fig 11
Fig 12
Fig 7
Fig 6

DEVICE FOR TREATING ANEURYSMS

FIELD OF THE INVENTION

The present invention relates to a device intended to treat lesions of the wall of blood vessels, in particular false aneurysms, by means of coagulation.

A classic cause of formation of false aneurysms is the puncture of a blood vessel. Following such a puncture, the wall of a vessel may be damaged and a pocket containing blood may form outside the vessel. Such a pocket is referred to in surgery as a "false aneurysm", by analogy with an aneurysm which results from deterioration of the walls of a vessel. In addition, the use of anticoagulants (common in the case of surgical interventions) favours the formation of false aneurysms.

BACKGROUND OF THE INVENTION

A known method for eliminating the pocket of a false aneurysm consists in pushing the pocket back by applying pressure from outside or by closing the channel supplying the pocket by controlled compression. Such a method can only be applied if the pocket is easily accessible, for example when the false aneurysm forms on a side of the vessel facing the patient's skin, or when the pressure is painful or ineffective.

Another known treatment method is to bring about the coagulation of the blood contained in the pocket, the consequence of which is necrosis of the said pocket.

The necrosed tissues are then eliminated naturally by the immune system, leaving only a very slight scar on the wall of the vessel.

Direct injection of coagulants is unfortunately ineffective and often contraindicated; this is because these products risk being entrained in large part by the blood stream, which is particularly harmful in the case of persons undergoing treatment.

A method with a more localized effect consists in inserting a filament made of totally inert biocompatible material which can be left in place without causing a detrimental reaction in the pocket, so as to form a ball therein.

However, this is a delicate operation; for the intervention to be effective, it may be necessary to introduce several meters of filament. The time needed to obtain sufficient coagulation is typically from one to two hours.

If the filament is to be recovered, the operation must then be repeated or must purely and simply be interrupted for a not inconsiderable period of time, which involves a substantial medical infrastructure.

If the filament is left in place, it may interfere with the proper conduct of subsequent operations performed on the same site or near this site, a fact which can be particularly inconvenient in the case of chronic diseases.

BRIEF SUMMARY OF THE INVENTION

The aim of the invention is to develop a device with which it is possible to treat false aneurysms by coagulation in a very short time compatible with the operating periods, and which is easy to maneuver and is reliable.

To this end, the subject of the invention is a device for provoking coagulation of a false aneurysm, which device comprises an introducer with valve and with removable needle, a filament which is able to be introduced as a ball into a pocket of a vascular lesion (where it will temporarily dwell) by folding up on itself therein, and a means of introduction which is able to introduce the said filament into the pocket through this introducer.

According to a first preferred embodiment, the filament is held via its proximal end in such a way that it can be withdrawn from the pocket after a defined time.

The filament is advantageously made up of a plurality of portions joined to one another via pliable zones.

The filament is preferably hollow and is bored longitudinally with a plurality of orifices through which it is possible locally to instill a coagulant into the pocket. p The filament can comprise a wire made of shape-memory metal treated in such a way that it has a substantially rectilinear shape at ambient temperature and a substantially rolled-up shape at the temperature of the body.

The filament advantageously comprises a core which is covered with an interlacing made of a thrombogenic material (for example, a braid).

In another embodiment, the filament is able to send an electric current sufficient to provoke electrocoagulation.

According to another advantageous embodiment, the filament comprises a core co-braided with a bundle of wires made of a thrombogenic material.

The material of the interlacing is chosen advantageously from between natural silk and Dacron®.

In another embodiment, the filament is made of bioabsorbable material with at thrombogenic effect.

The material of the filament has, for example, a minimum absorption period of 20 minutes.

In a preferred manner, the means for introducing the filament comprises an envelope which can be torn longitudinally and in which the filament is accommodated.

The means for introducing the wire can also comprise a guide along which the filament is applied in a detachable manner or a rod with an end in the form of an elastically deformable loop which is able to introduce the filament into the pocket by way of a reciprocating movement.

The filament is preferably radiopaque.

Using the device according to the invention, it is possible to reduce the time needed for coagulation to a few minutes, which means that it is possible to perform an operation practically without interruption, which benefits both the practitioner and the patient.

The length of the filament is considerably shorter in relation to the empirical method described above, a fact which reduces the time needed for the introduction and diminishes the risks associated with the operation.

Since the filament has an entirely localized effect in the pocket of the aneurysm, it is no longer necessary to inject coagulants in liquid form, and so there is no longer a risk of these products disseminating through the body.

Trials have shown that treatment using the device according to the invention is reliable since the false aneurysm thus coagulated presents a very low risk of relysis after withdrawal or elimination of the wire at the end of a predetermined time.

BRIEF DESCRIPTION OF THE SEVERAL VIEWS

Other characteristics are advantages of the invention will become clearer from the following description of several particular embodiments, which are given by way of non-limiting examples and with reference to the attached diagrammatic drawings, in which:

FIG. 6 is an enlarged view of an embodiment of a device according to the invention using a hollow folding catheter in accordance with the invention;

FIG. 7 is a diagrammatic view of an embodiment involving a wire made of shape-memory metal;

FIG. 11 and 12 are diagrammatic views of another embodiment of a filament according to the invention.

DETAILED DESCRIPTION OF THE DRAWINGS

Figure 1:
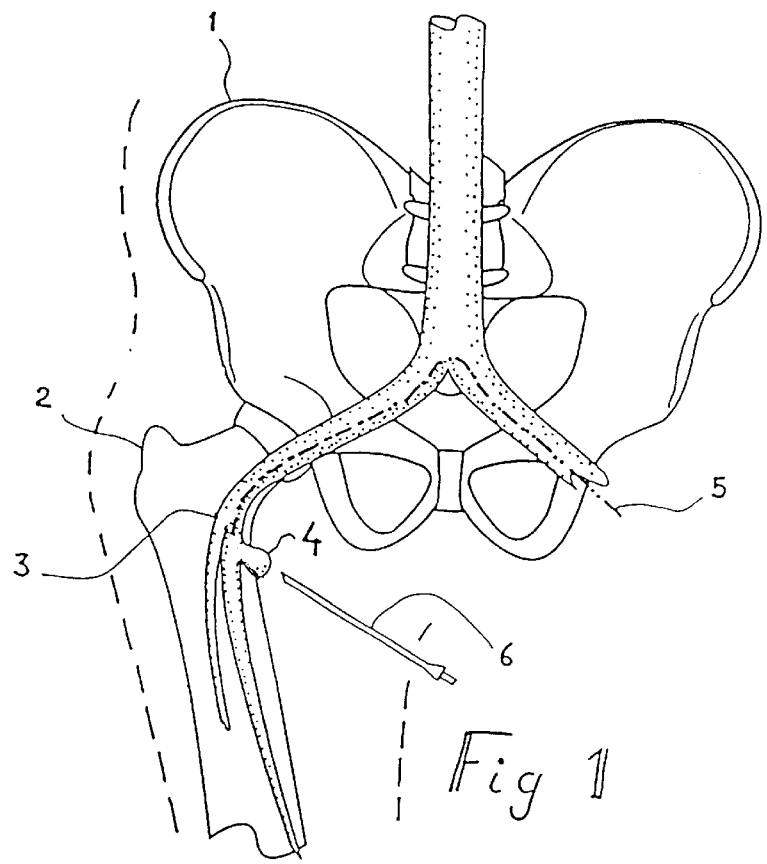
FIG. 1 is a general view of an aneurysm site.
Figure 2:
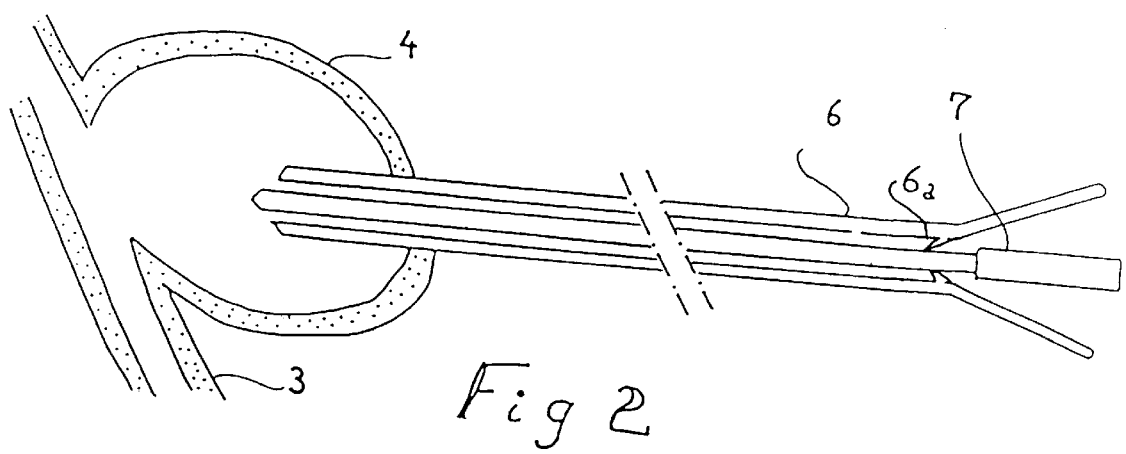
FIG. 2 is an enlarged view showing a device according to the invention during its introduction into the pocket of a false aneurysm.

FIG. 1 shows a subject's pelvis 1, on which a femur 2 articulates, and it also shows a femoral artery 3 presenting a pocket 4 of a false aneurysm. A guide catheter 5 is inserted by the contralateral route into the femoral artery 3 in such a way that its distal end is in proximity to the pocket 4 of the false aneurysm in order to control the puncture point. FIG. 2 shows the introducer 6, having a valve 6a, of a device according to the invention, in which introducer 6 there is accommodated a puncture needle 7 inserted into the pocket 4. To facilitate the puncture of the false aneurysm of the pocket 4, the introducer 6 is preferably equipped with one or more radiopaque markers (not shown). The introducer 6 is substantially tubular and typically has a length of about 10 cm and an external diameter varying form 1.3 to 2 mm.

Figure 5:
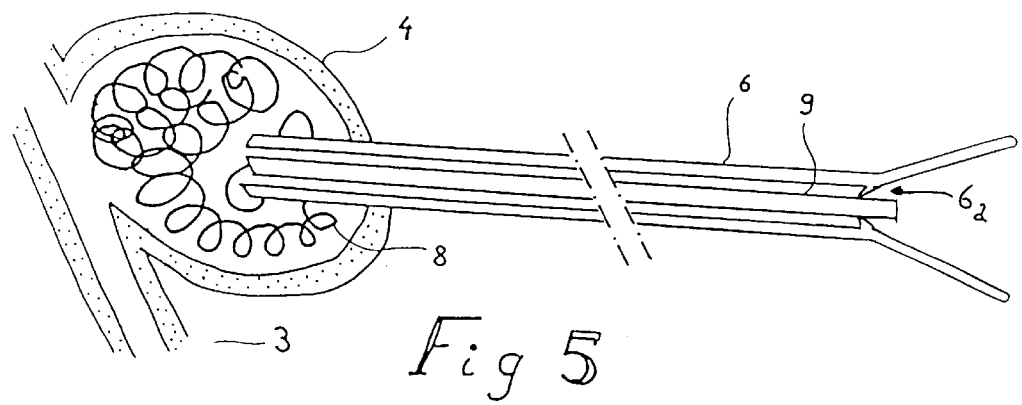
FIG. 5 is a view analogous to FIG. 4, showing the pocket of the false aneurysm at the end of the introduction phase.
Figure 3:
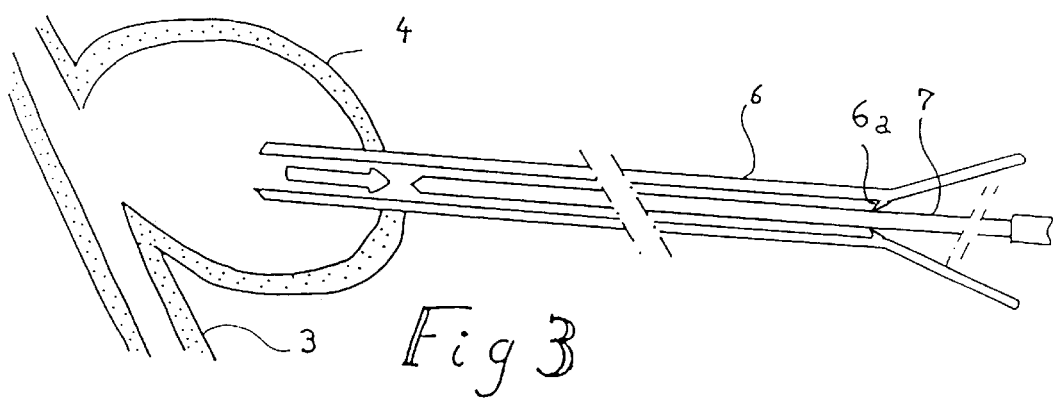
FIG. 3 is an enlarged view of the device in FIG. 1, after withdrawing the needle of the introducer.
Figure 4:
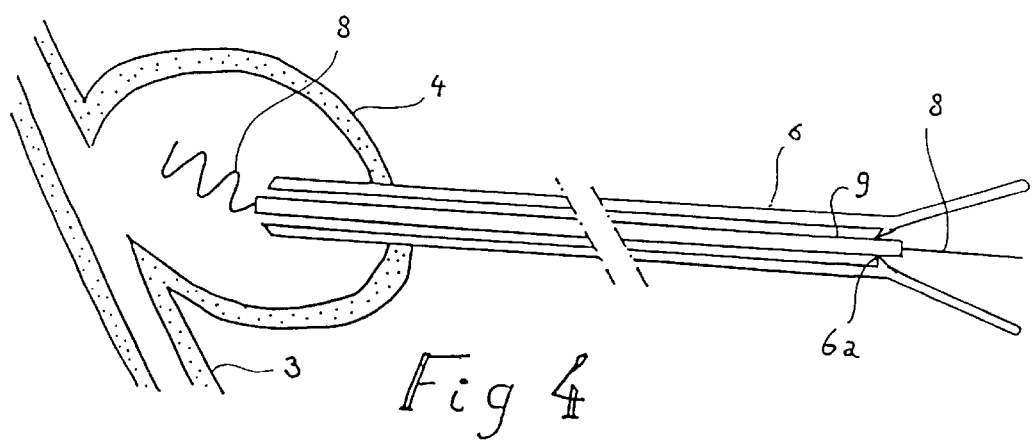
FIG. 4 is an enlarged view of the same device at the moment of the introduction of a filament into the pocket.

Once the distal end of the entroducer 6 has been introduced into the pocket 4, the needle 7 can be withdrawn, as can be seen in FIG. 2. A part of the blood filling the pocket 4 may be drained at this stage through the introducer 6 by keeping its valve open. A filament 8 having characteristics which will be described in more detail below can then be introduced through the introducer 6 into the pocket 4, by a means of introduction 9 as is indicated diagrammatically in FIG. 4. This filament 8 has the characteristic of easily rolling up on itself to form a sort of ball in the pocket 4, as can be seen in FIG. 5, the effect of which, combined with other properties described below, is rapidly to provoke the coagulation of the blood contained in the pocket 4. After a defined time, of the order of a few minutes (at most of the order of 20 minutes), the filament 8, having exerted its effect, will be removed as described below.

A first embodiment of a filament 18 according to the invention and of its means of introduction 19 is shown in FIG. 5. The filament 18 is made up of a plurality of portions 20 joined to one another via pliable zones 22, each portion 20 having a defined length, for example of the order of 5 to 10 mm, in order to permit pleating in a concertinaed (or W-shaped) fashion inside the pocket 4 as soon as it leaves the introducer 6. Such a filament 18 is preferably made of an elastic material, such as a metal or plastic wire with a spring action. In the embodiment shown in FIG. 6, the filament 18 is additionally hollow and has a plurality of orifices 24 in such a way as to allow localized installation or injection or coagulant via the proximal end of the filament 18, this product flowing through the orifices 24 locally into the pocket 4 so as to accelerate the coagulation of the false aneurysm. The proximal end of the filament 18 remains held in the proximal part of the device. The operator can easily control any sweeping from the pocket 4 over time, before proceeding to withdraw the filament once the coagulation is ensured. The means of introduction 19 is in this case a rigid sheath which, while still allowing the filament 18 to slide, prevents the latter from folding up on itself prematurely before it leaves the introducer.

FIG. 7 shows another embodiment 28 of the filament 8 according to the invention; in this embodiment, the filament comprises a core 30 formed form a shape-memory metal wire (such as a Nitinol wire). The filament 28 is introduced through the introducer 6 into the pocket 4, along a portion of hollow catheter 9. The metal wire from which the core 30 is formed has undergone a preliminary heat treatment giving it a transformation threshold slightly below the temperature of the human body; it has a first substantially rectilinear shape at ambient temperature (outside the patien's body); however, as soon as its temperature exceeds the transition threshold assigned to it, or in this case as soon as it passes beyond the tip of the introducer 6, it immediately adopts a curved shape and rolls up in the manner of a spring inside the pocket 4. With the proximal end of the filament 28 being held in the device outside the body, the operator can withdraw it after coagulation of the pocket 4 after a defined time. As it is being withdrawn, the filament 28 recovers its substantially rectilinear shape, which reduces the friction with the catheter. The two embodiments which have been described above with reference to FIGS. 6 and 7 can be combined, the filament 8 then having a roughly epicycloidal appearance in the pocket 4.

FIG. 7 shows an embodiment of the filament according to the invention which combines with the core 30 a braided sheath 32 made of a material with a thrombogenic action.

This sheath 32 can be made in particular of silk (inter alia, of spider silk) or of Dacron®. The naturally thrombogenic effects of these materials are exacerbated here by the high surface area developed in the device according to the invention. In addition, the material of the sheath can be impregnated with various pharmacological substances with a thrombogenic effect. Such substances can also be integrated or grafted chemically into the structure of the braided yarns forming the sheath 32.

According to another embodiment, the yarns are not braided around a core but are co-braided or twisted with the latter. In the embodiment represented in FIGS. 11 and 12, the core 40, after introduction into the pocket 4, can cause the bundle of yarns 42 to loosen, as shown in FIG. 12.

In this embodiment, the core 40 is also hollow, which, as is shown in FIG. 6, allows localized installation of coagulants. The core 40 also comprises a stiffening means, in this case a movable rod which can be actuated from the proximal end of the filament.

The guide means used can have various forms; it can, as in the embodiments shown in the preceding figures, involve a portion of greater or lesser length of rigid sheath.

Figure 8:
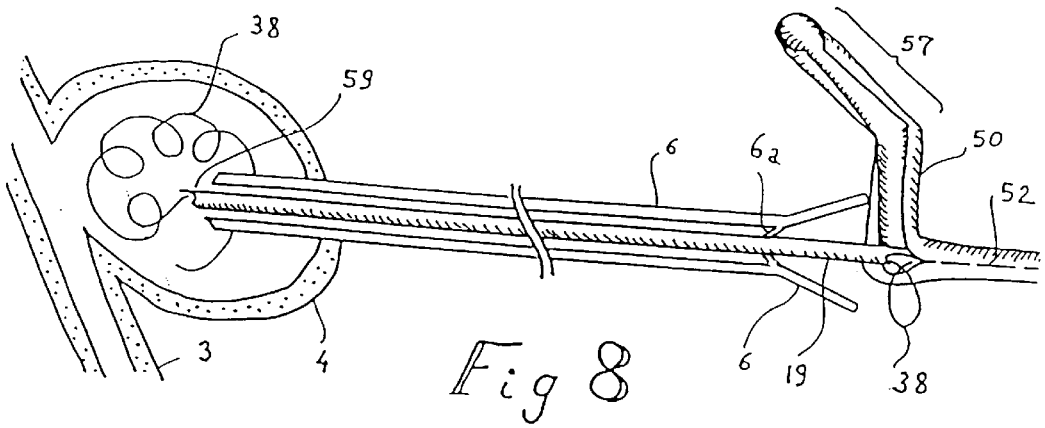
FIG. 8 is an enlarged view of an embodiment employing a longitudinally tearable or peelable sheath.
Figure 9:
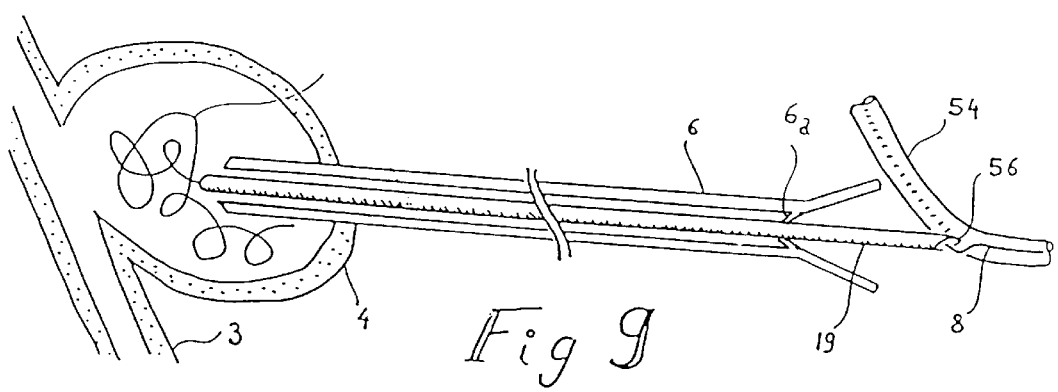
FIG. 9 is a view analogous to FIG. 6, in which the filament is bonded detachably to the outside of a guide.
Figure 10:
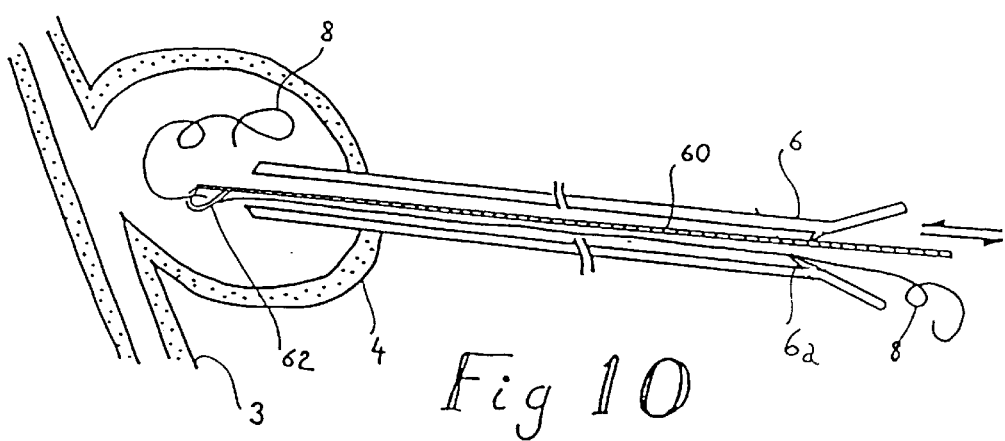
FIG. 10 is a view analogous to FIG. 8, with a means of introduction having a reciprocating movement.

FIGS. 8 to 10 show various alternative forms of this guide means, facilitating the manipulation of filaments 5, 18 according to the invention. It is thus possible here, in conjunction with a catheter 9, to use a longitudinally tearable sheath 50 50 (a so-called "peelable" sheath) which surrounds the filament 8. This sheath, having one or more longitudinal tear lines 52, splits open as the filament 8 is being introduced into the introducer 6. If the filament 8 has a very low rigidity, it can also be applied detachably by adhesive to the outer surface of a guide support 54, especially along a groove. A suitable separating means, such as a beveled rigid 56, detaches the filament from its guide support 54 on entry into the introducer 6, as is represented in FIG. 9.

In the embodiment illustrated in FIG. 8, the filament 38 is made of a bioabsorbable material, which allows it to be absorbed automatically after a defined dwell time inside the pocket 4. This filament 38 is accommodated inside a succession of catheter portions 57 which are longitudinally tearable 50.

Segmentation into portions 57 permits easy manipulation of the filament 38 whose length can be easily estimated on the basis of the number of portions used.

As the material used is bioabsorbable, it is not necessary here to withdraw the filament, and it suffices to detach it from the means of introduction 19. Consequently, a separating means (in this case a beveled ridge 59) is provided at the distal end of the introducer 6. By exerting a relative traction on the means of introduction 19, the operator causes the filament 38 to separate. The operation can be repeated several times since the filament 38 can be introduced without inconvenience in noncontinuous form.

FIG. 10 shows another means of introducing the filament 8, consisting here of a metal rod 60 which is provided, at its distal end, with a lasso-shaped deformable loop 62.

The distal end of a filament 8 of the invention having been introduced into this loop 62, it suffices to insert the rod 60 into the introducer 6 and to effect a to- and fro-movement with the metal rod 60, which entrains the filament 8 on its forward movement and releases it upon its return movement.

The various means of introduction which have been described above can of course be used in combination with the form of filament 8, 18, 28, 38 which is most appropriate for the case to be treated (in particular depending on the dimensions and the position of the pocket 4 of the false aneurysm).

What is claimed is:

1. A device for treating an aneurysm by means of coagulation within a tissue pocket of said aneurysm, comprising:
an introducer having alumen therein, with a needle being removably disposed in said lumen;
a filament which is adapted to be introduced into the pocket of said aneurysm, where said filament will temporarily dwell, and to roll up on itself therein; and
a filament delivery device, adapted for insertion in said lumen in place of said needle to introduce said filament into the pocket through the introducer.

2. A device according to claim 1, wherein said filament delivery device is adapted to retain at least a proximal end of the filament such that said filament delivery device can withdraw said filament form the pocket after a defined time.

3. A device according to claim 2, wherein the filament is made up of a plurality of portions joined to one another by pliable zones.

4. A device according to claim 3, wherein said portions are straight portions.

5. A device according to claim 2, wherein the filament is hollow and is bored longitudinally with a plurality of orifices therein.

6. A device according to claim 5, wherein the plurality of orifices establishes communication between the pocket and a hollow portion of the filament, the filament having a proximal end coupled to a coagulant feeding device.

7. A device according to claim 2, wherein the filament comprises a wire made of shape-memory metal treated in such a way that it has a substantially rectilinear shape at ambient temperature and a substantially rolled-up shape at the temperature of a body.

8. A device according to claim 7, wherein the filament comprises a core which is covered with an interlacing made of a thrombogenic material.

9. A device according to claim 8, wherein the covering is a braid.

10. A device according to claim 8, wherein the material of the interlacing is chosen from between natural silk and polyethylene fibers.

11. A device according to claim 7, wherein the filament comprises a core co-braided with a bundle of wires made of a thrombogenic material.

12. A device according to claim 2, wherein the filament comprises a core which is covered with an interlacing made of a thrombogenic material.

13. A device according to claim 12, wherein the covering is a braid.

14. A device according to claim 13, wherein the material of the interlacing is chosen from between natural silk and polyethylene fibers.

15. A device according to claim 2, wherein the filament comprises a core co-braided with a bundle of wires made of a thrombogenic material.

16. A device according to claim 2, wherein the filament delivery device comprises an envelope which can be torn longitudinally and in which the filament is accommodated.

17. A device according to claim 16, wherein the envelope is disposed proimate to a proimal end of said filament delivery device.

18. A device according to claim 2, wherein the filament delivery device comprises a guide along which the filament is applied in a detachable manner.

19. A device according to claim 18, wherein the guide is disposed proximate to a proximal end of said filament delivery device.

20. A device according to claim 2, wherein the filament delivery device comprises a rod having an end in the form of an elastically deformable loop which is able to introduce the filament into the pocket by a reciprocating movement.

21. A device according to claim 20, wherein the loop is disposed proximate to a distal end of said introducer, and is adapted to pull the filament into the pocket by said reciprocating movement.

22. A device according to claim 21, wherein said guide comprises an envelope that is adapted to accommodate the filament and to be torn longitudinally.

23. A device according to claim 1, wherein the filament is made of bioabsorbable material with a thrombogenic effect.

24. A device according to claim 23, wherein the material of the filament has a minimum absorption period of 20 minutes.

25. A device according to claim 1, wherein the filament delivery device comprises an envelope which can be torn longitudinally and in which the filament is accommodated.

26. A device according to claim 25, wherein the envelope is disposed proximate to a proimal end of said filament delivery device.

27. A device according to claim 1, wherein the filament delivery device comprises a guide along which the filament is applied in a detachable manner.

28. A device according to claim 27, wherein the guide is disposed proximate to a proimal end of said filament delivery device.

29. A device according to claim 1, wherein the filament delivery device comprises a rod having an end in the form of an electrically deformable loop which is able to introduce the filament into the pocket by way of a reciprocating movement.

30. A device according to claim 29, wherein the loop is disposed proximate to a distal end of said introducer, and is adapted to pull the filament into the pocket by said reciprocating movement.

31. A device according to claim 1, wherein the filament is radiopaque.

32. A device according to claim 1, wherein the filament is able to send an electric current sufficient to provoke electrocoagulation.

33. A device according to claim 1, wherein said introducer comprises a valve.

34. A device according to claim 1, wherein said introducer is a separated tubular introducer.

35. A device according to claim 1, wherein said filament delivery device comprises a guide disposed proximate to a proximal end of said filament delivery device, the filament being detachably applied to the guide.

36. A method for treating aneurysms comprising the following steps:
   introducing in a pocket of an aneurysm an introducer having a removable needles;
   removing the needle;
   inserting a filament delivery device in the introducer;
   introducing a thrombogenic bendable filament through the introducer into the pocket;
   causing the filament to form a ball inside the pocket;
   allowing the filament to provoke coagulation of the blood contained in the pocket; and
   removing the filament.

37. A method according to claim 36, wherein said introducer comprises a valve.

38. A method according to claim 36, wherein:
   the filament removing step removes the filament through the introducer and filament delivery device; and
   the method further comprises the steps of:
      removing the filament delivery device; and
      removing the introducer.

39. A device for treating an aneurysm by means of coagulation within a tissue pocket of said aneurysm, comprising:
   an introducer comprising a removable needle;
   a filament which is adapted to be introduced into the pocket of said aneurysm, where said filament will temporarily dwell, and to roll up on itself therein; and
   a filament delivery device, adapted to introduce said filament into the pocket through the introducer, and comprising an envelope which can be torn longitudinally and in which the filament is accommodated.

40. A device according to claim 39, wherein the envelope is disposed proximate to a proximal end of said filament delivery device.

41. A device according to claim 40, wherein the envelope is disposed proximate to a proximal end of said filament delivery device.

42. A device for treating an aneurysm by means of coagulation within a tissue pocket of said aneurysm, comprising:
   an introducer comprising a removable needle;
   a filament which is adapted to be introduced into the pocket of said aneurysm, where said filament will temporarily dwell, and to roll up on itself therein; and
   a filament delivery device, adapted to introduce said filament into the pocket through the introducer, and to retain at least a proximal end of the filament such that said filament delivery device can withdraw said filament from the pocket after a defined time, the filament delivery device comprising an envelope which can be torn longitudinally and in which the filament is accommodated.

43. A device for treating an aneurysm by means of coagulation within a tissue pocket of said aneurysm, comprising:
   an introducer comprising a removable needle;
   a filament which is adapted to be introduced into the pocket of said aneurysm, where said filament will temporarily dwell, and to roll up on itself therein; and
   a filament delivery device, adapted to introduce said filament into the pocket through the introducer, said filament delivery device comprising a guide disposed proximate to a proximal end of said filament delivery device, the filament being detachably applied to the guide, said guide comprising an envelope that is adapted to accommodate the filament and to be torn longitudinally.

* * * * *